United States Patent [19]

Tischlinger

[11] 4,051,851

[45] Oct. 4, 1977

[54] DIAPHRAGM ASSEMBLY FOR A MEDICAMENT DISPENSING UNIT

[76] Inventor: Edward A. Tischlinger, 7 Froghollow Road, East Lyme, Conn. 06333

[21] Appl. No.: 672,392

[22] Filed: Mar. 31, 1976

[51] Int. Cl.$^2$ .............................................. A61M 5/00
[52] U.S. Cl. ...................... 128/218 NV; 128/218 DA
[58] Field of Search .... 128/218 NV, 218 D, 218 DA, 128/221, 272, 220, 215, 216

[56] References Cited

U.S. PATENT DOCUMENTS

| | | | |
|---|---|---|---|
| 3,387,609 | 6/1968 | Shields | 128/218 NV |
| 3,391,695 | 7/1968 | Sarnoff | 128/218 NV |
| 3,424,155 | 1/1969 | Sarnoff | 128/218 NV |
| 3,710,794 | 1/1973 | Shields | 128/218 D X |
| 3,768,473 | 10/1973 | Shields | 128/218 NV |

Primary Examiner—John D. Yasko
Attorney, Agent, or Firm—Y. Judd Azulay

[57] ABSTRACT

A medicament dispensing unit having a cylindrical barrel closed at one end by a slidable plunger is provided at the other end with a diaphragm assembly including a flexible wall defining a medicament chamber between the plunger and flexible wall. A needle is positioned in spaced relation to the flexible wall whereby movement of the plunger will cause the medicament to flex the flexible wall toward the needle which will then pierce the wall to establish fluid communication between the medicament chamber and the area at the other end of the needle. A finger grip is located on the plunger end of the barrel while a nose cap assembly is affixed to the diaphragm end of the barrel.

4 Claims, 2 Drawing Figures

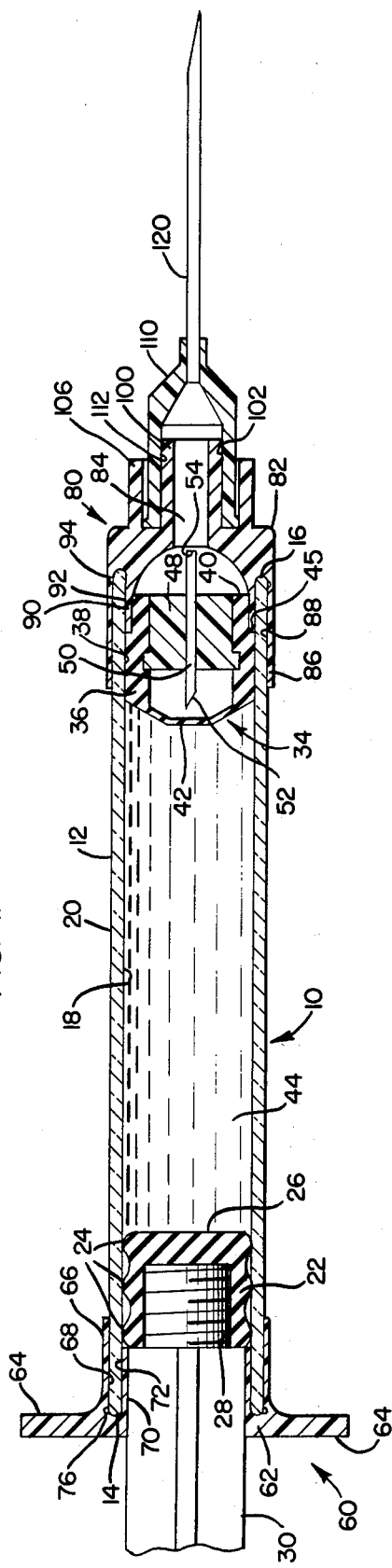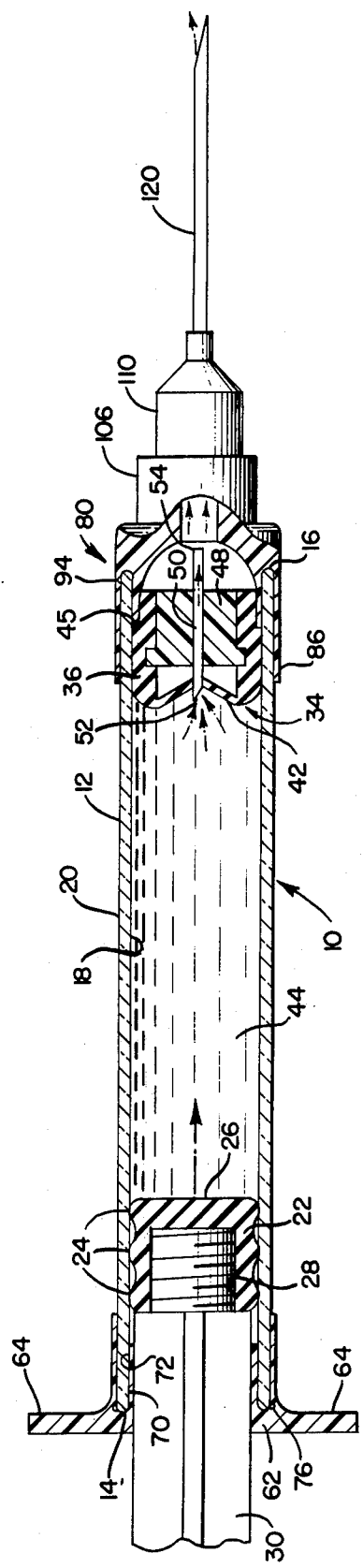

DIAPHRAGM ASSEMBLY FOR A MEDICAMENT DISPENSING UNIT

SUMMARY OF THE INVENTION

The field of medicament dispensing apparatus has in recent years become very highly developed; for example, for nearly every type of dispensing need there has been provided a specific dispenser. To produce such dispensing units, which are generally disposable, at a reasonable cost requires that they be made interchangeable as often as possible.

In view of the foregoing, it is an object of this invention to provide a diaphragm assembly suitable for use in many types of medicament dispensing units.

It is another object of this invention to provide a diaphragm assembly for a medicament injector wherein the injector includes a cylindrical barrel closed at one end by a slidable plunger and at the other end by a diaphragm assembly. A finger grip may be provided on the plunger end of the barrel while a nose cap assembly is mounted on the diaphragm end of the barrel.

It is yet another object of this invention to provide a diaphragm assembly as in the preceding objects wherein the diaphragm assembly includes a flexible wall defining a medicament chamber between the plunger and the flexible wall; a needle is positioned in spaced relation to the flexible wall whereby upon movement of the plunger toward the flexible wall said wall will flex toward the needle and be pierced thereby to establish fluid communication between the medicament chamber and the area on the other side of the diaphragm assembly.

It is a still further object to provide a medicament dispenser comprising a cylindrical barrel having a front end and a rear end, a plunger slidably carried in the rear end of the barrel to sealingly close off the rear end of the barrel, a diaphragm assembly mounted in the front end of the barrel to close off that end of the barrel, the improvement residing in the diaphragm assembly which assembly comprises a body sized to sealingly fit within the barrel, said body having a hollow portion facing the rear end of the barrel, a flexible wall closing off the hollow portion to form a medicament chamber between said flexible wall and the plunger, a needle carried by the body with its end spaced from the flexible wall, said needle being adapted to pierce the flexible wall when said wall is flexed inwardly under the action of the moving plunger to establish fluid communication between the medicament chamber and the needle.

IN THE DRAWING

FIG. 1 is a longitudinal sectional view of a medicament dispensing unit provided with the diaphragm assembly of this invention, wherein the unit is in condition for immediate use, and FIG. 2 is a longitudinal sectional view of the dispensing unit after the plunger has moved forward to flex the diaphragm wall inwardly for piercing by the needle to allow medicament to flow therethrough.

DETAILED DESCRIPTION OF THE INVENTION

One type of unit suitable for use with the diaphragm assembly of this invention is illustrated in FIGS. 1 and 2, wherein the medicament dispenser 10 comprises a cylindrical glass barrel 12 having an open rear end 14 and an open forward end 16 and an inner surface 18 and an outer surface 20. A rubber plunger 22 is sealingly and slidably carried in the rearward portion of the barrel 12. The plunger 22 is provided with a plurality of circumferential ridges 24 which act as sealing means for the plunger. The forward end of the plunger is closed by an end face 26 while the rear end has a threaded opening 28 adapted to threadedly mount a plunger rod 30.

The diaphragm assembly 34 is positioned in the forward end portion of the barrel 12 and comprises a cylindrical body 36 having an outer surface 38 snugly engaging the inner surface 18 of the barrel 12. The body 36 has an open forward end 40 and a rear end closed by a flexible end wall 42 to form a medicament chamber 44 between said flexible end wall and end 26 of the plunger 22. The forward portion of the outer surface 38 of the diaphragm body 36 is cut away to a small depth to form a shoulder 45. A needle mount 48 is fitted within the diaphragm body 36 and fixedly carries needle 50 having its rear pointed end 52 spaced from the flexible end wall 42. The forward end 54 of the needle 50 is so positioned that fluid communication is established with the forward end of the barrel 12.

The finger grip 60 is mounted on the rear end of the barrel 12, said finger grip comprises a circular body portion 62 having a pair of finger grip elements 64, 64 extending diametrically outwardly from said body and generally perpendicular to the longitudinal axis of the glass barrel 12. An outer circumferential wall 66 extends forwardly from the finger grip body 62 and is sized such that the inner surface 68 of the wall 66 snugly engages the outer surface 20 of the glass barrel 12. Similarly, a circular inner wall 70 extends forwardly from the finger grip body 62 and is sized so that its outer surface 72 will snugly engage the inner surface 18 of the glass barrel 12. It is by means of the engagement of the finger grip inner and outer walls 70 and 66, respectively, with the confronting surfaces of the glass barrel 12 that the finger grip is retained thereon. On the inner side where the finger grip body 62 and the outer wall 66 meet there is provided a slight undercut 76 to give a small amount of flexibility to the body 62 and the outer wall 66 during the insertion of the glass barrel 12 into the space between the outer and inner walls, 66 and 70, respectively.

One type of nose cap suitable for use is shown in FIG. 1 wherein the nose cap 80 is mounted on the forward end of the barrel 12, said nose cap includes a circular body portion 82 having a central opening 84 therethrough. An outer circumferential wall 86 extends rearwardly from the circular body portion 82 and is sized so that the inner surface 88 of the wall 86 snugly engages the outer surface 20 of the glass barrel 12. Similarly, a circular inner wall 90 extends rearwardly from the circular body portion 82 and is sized such that the outer surface 92 of the inner wall 90 snugly engages the inner surface 18 of the glass barrel 12. Here again, it is by means of the engagement of the nose cap 80, inner and outer walls 90 and 86, respectively, of the circular body portion 82 with the confronting surfaces on the glass barrel 12 that the nose cap 80 is held thereon. As in the finger grip 60, a slight undercut 94 is formed where the body 82 and outer wall 86 meet to provide a small amount of flexibility for easing the assembly of the nose cap onto the barrel 12. It should be noted that the inner wall 90 is shorter than the outer wall 86 and that its end abuts the shoulder 44 on the diaphragm body 36 to position the diaphragm assembly 34.

A cylindrical bearing 100 projects forwardly from the circular body portion 82 with its longitudinal axis in alignment with the opening 84 in the aforesaid body portion 82. The outer surface 102 of the bearing 100 is provided with a taper corresponding to the standard Luer Lok Taper. Additionally, an internally threaded collar 106 extends outwardly and forwardly from the circular body portion 82 to surround the cylindrical bearing 100. The bearing 100 and collar 106 provide mounting means for various cannula assemblies. More specifically, cannula hub 110 whose inner surface 112 has a taper coinciding with that on the outer surface 102 of the bearing 100 fits on said bearing and supports cannula 120 affixed to the forward end of the hub 110.

In use, the medicament dispenser 10 as shown in FIG. 1 has a cannula 120 of the desired gauge assembled onto the cylindrical nose cap bearing 100 and the plunger rod 30 is suitably attached to the plunger 22. Forward movement of the plunger 22 under force exerted by plunger rod 30 forces the medicament in chamber 44 forwardly, thus causing the diaphragm assembly end wall 42 to flex forwardly toward the end 52 of needle 50. As shown in FIG. 2, continued flexing in the forward direction causes the needle point 52 to pierce end wall 42 and extablish fluid communication between chamber 44 and the cannula 120 for exiting of the medicament. Forward movement of the plunger 22 continues until ejection is complete.

The diaphragm assembly 34 could take many shapes and yet provide the specific function set forth previously in the specification. The main requirement is that the flexible wall 42 must be space from the needle 50 so that when the plunger 22 moves toward the front end of the barrel 12 the wall will be flexed so that it will come in contact with and be pierced by the needle 50. This type of diaphragm assembly readily meets all mass production requirements and is also quite economical with reqard to requisite materials.

It is claimed that:

1. In a medicament dispenser comprising a cylindrical barrel having a front and a rear end, a plunger slidably carried in the rear end of the barrel to sealingly close off the rear end of the barrel, a diaphragm assembly mounted in the front end of the barrel to close off that end of the barrel, the improvement residing in the diaphragm assembly which assembly comprises a body sized to sealingly fit within the barrel, said body having a hollow portion facing the rear end of the barrel, a flexible wall closing off the hollow portion to form a medicament chamber between said flexible wall and the plunger, a needle monted by means fitted within the diaphragm body and carried by the body with its end spaced from the flexible wall, said needle being spaced from the flexible wall and adapted to pierce the flexible wall said wall is flexed inwardly under the action of the moving plunger to establish fluid communication between the medicament chamber and the needle.

2. In a medicament dispenser comprising a cylindrical barrel having a front and a rear end, a plunger slidably carried in the barrel adjacent the rear end thereof, said plunger sealingly closing off the rear end of the barrel, a diaphragm assembly having a hollow cylindrical body mounted in the barrel adjacent the front end thereof, a nose cap assembly fitting on the front end of the barrel beyond the diaphragm assembly, said nose cap assembly including a dispensing member in fluid communication with diaphragm assembly, the improvement residing in the diaphragm assembly which assembly comprises a body sized to sealingly fit within the barrel, a flexible wall fitting over the end of the body facing the plunger to form said hollow area, a medicament chamber being formed between the plunger and the flexible wall, a needle mounted by means fitted within the diaphragm body so that one of its ends is spaced from the flexible wall, said needle being adapted to pierce the flexible wall when said wall flexes inwardly under the action of the moving plunger to establish fluid communication between the medicament chamber and the dispensing member in the nose cap assembly.

3. The invention as set forth in claim 2 and wherein the flexible wall is bowed outwardly toward the rear end of the berrel to form the hollow area.

4. A diaphragm assembly adapted for mounting in a cylindrical barrel to act as a seal and as a means of fluid communication between the spaces on opposite sides of the seal formed by the diaphragm assembly, said diaphragm assembly comprising: a body sized to sealingly fit within the barrel, a flexible wall fitting over one end of the body to form a hollow space therebetween, a needle mounted by means within the diaphragm body so that one of its ends is positioned in the hollow space adjacent the flexible wall, said needle being adapted to pierce the flexible wall when the wall flexes inwardly toward the needle to thereby establish fluid communication between the spaces on opposite sides of the seal.

* * * * *